(12) United States Patent
Hermens et al.

(10) Patent No.: US 9,115,373 B2
(45) Date of Patent: Aug. 25, 2015

(54) USE OF AAV REPLICATION MACHINERY FOR IMPROVED PROTEIN PRODUCTION

(75) Inventors: Wilhelmus Theodorus Johannes Maria Christiaan Hermens, Almere (NL); Yvet Noordman, Utrecht (NL); Andrew Christian Bakker, Almere (NL)

(73) Assignee: UNIQURE IP B.V., Amsterdam (NL)

( * ) Notice: Subject to any disclaimer, the term of this patent is extended or adjusted under 35 U.S.C. 154(b) by 690 days.

(21) Appl. No.: 12/679,144

(22) PCT Filed: Sep. 18, 2008

(86) PCT No.: PCT/NL2008/050613
§ 371 (c)(1),
(2), (4) Date: Aug. 30, 2010

(87) PCT Pub. No.: WO2009/038462
PCT Pub. Date: Mar. 26, 2009

(65) Prior Publication Data
US 2011/0119777 A1    May 19, 2011

Related U.S. Application Data

(60) Provisional application No. 60/973,517, filed on Sep. 19, 2007.

(30) Foreign Application Priority Data

Sep. 19, 2007  (EP) .................................... 07075817

(51) Int. Cl.
*C12P 21/06*    (2006.01)
*C12N 5/07*    (2010.01)
*C12N 15/86*    (2006.01)

(52) U.S. Cl.
CPC ............. *C12N 15/86* (2013.01); *A01K 2217/05* (2013.01); *C12N 2710/14143* (2013.01); *C12N 2830/00* (2013.01)

(58) Field of Classification Search
CPC ............................ C12N 15/86; C12N 2830/00
USPC ................................................ 435/69.1, 348
See application file for complete search history.

(56) References Cited

U.S. PATENT DOCUMENTS

| 6,156,303 A * | 12/2000 | Russell et al. ............... 424/93.2 |
| 2002/0110837 A1 | 8/2002 | Chao et al. |
| 2003/0082144 A1 | 5/2003 | Chao |
| 2005/0112095 A1 * | 5/2005 | Hsu et al. ..................... 424/93.2 |

FOREIGN PATENT DOCUMENTS

| WO | 98/45462 | 10/1998 |
| WO | 9845462 | 10/1998 |

OTHER PUBLICATIONS

Sollerbrant et al., 2001, J. General Virology, vol. 82, pp. 2051-2060. Cited on IDS.*
Palombo et al., 1998, J. Virology, June, pp. 5025-5034.*
Berger et al., 2004, Nature Biotechnology, vol. 22(12), pp. 1583-1587.*
Urabe et al. (2002, Human Gene Therapy, vol. 13, pp. 1935-1943).*
Ikonomou et al. (2003, Appl. Microbiol. Biotechnol., vol. 62, pp. 1-20).*
Zeng et al., "Baculoviral vector-mediated transient and stable transgene expression in human embryonic stem cells," Stem Cells, 2007, 25:1055-1061.
Sollerbrant et al.,"A novel method using baculovirus-mediated gene transfer for production of recombinant adeno-associated virus vectors," Journal of General Virolog, 2001, 82:2051-2060.
Mannix, C: "A Brief Overview of the Baculovirus Expression System in Insect and Mammalian Cells," In: Medicines from Animal Cell Culture, G. Stacey and J. Davis, eds,, John Wiley & Sons, Ltd., U.S., 2007.
Hu,"Baculovirus as a highly efficient expression vector in insect and mammalian cells," Acta Pharmacologica Sinica, 2005, 26:405-416.
L. Li, EK. Dimitriadis, Y. Yang, J. Li, Z. Yuan, C. Qiao, C. Beley, RH Smith, L. Garcia, RM Kotin. Production and Characterization of Novel Recombinant Adeno-Associated Virus Replicative-Form Genomes: A Eukaryotic Source of DNA for Gene Transfer. PLoS ONE 8(8) e69879 (1-13) Aug. 2013.

* cited by examiner

*Primary Examiner* — Anoop Singh
*Assistant Examiner* — David A Montanari
(74) *Attorney, Agent, or Firm* — Browdy and Neimark, PLLC

(57) ABSTRACT

The present invention provides a method for enhanced production of a gene product of interest in a cell, using the AAV replication machinery. The present invention further relates to a cell for use in the method of the invention and a non-human transgenic animal or a transgenic plant comprising a cell of the invention.

7 Claims, 2 Drawing Sheets

SEQUENCE LISTING

<160> NUMBER OF SEQ ID NOS: 3

<210> SEQ ID NO 1
<211> LENGTH: 146
<212> TYPE: DNA
<213> ORGANISM: adeno-associated virus 2

<400> SEQUENCE: 1

```
gggccactc cctctctgcg cgctcgctcg ctcactgagg ccgcccgggc aaagcccggg         60
cgtcgggcga cctttggtcg cccggcctca gtgagcgagc gagcgcgcag agagggagtg        120
gccaactcca tcactagggg ttcctc                                             146
```

```
<210> SEQ ID NO 2
<211> LENGTH: 1876
<212> TYPE: DNA
<213> ORGANISM: adeno-associated virus 2
<220> FEATURE:
<221> NAME/KEY: CDS
<222> LOCATION: (11)..(1876)
<223> OTHER INFORMATION: Rep78
<220> FEATURE:
<221> NAME/KEY: misc_feature
<222> LOCATION: (683)..(1876)
<223> OTHER INFORMATION: coding sequence Rep 52

<400> SEQUENCE: 2
```

```
cgcagccgcc atg ccg ggg ttt tac gag att gtg att aag gtc ccc agc          49
            Met Pro Gly Phe Tyr Glu Ile Val Ile Lys Val Pro Ser
              1               5                  10 gac ctt gac gag cat ctg ccc ggc att tct gac agc ttt gtg aac tgg         97
Asp Leu Asp Glu His Leu Pro Gly Ile Ser Asp Ser Phe Val Asn Trp
 15                  20                  25 gtg gcc gag aag gaa tgg gag ttg ccg cca gat tct gac atg gat ctg        145
Val Ala Glu Lys Glu Trp Glu Leu Pro Pro Asp Ser Asp Met Asp Leu
 30                  35                  40                  45 aat ctg att gag cag gca ccc ctg acc gtg gcc gag aag ctg cag cgc        193
Asn Leu Ile Glu Gln Ala Pro Leu Thr Val Ala Glu Lys Leu Gln Arg
                 50                  55                  60 gac ttt ctg acg gaa tgg cgc cgt gtg agt aag gcc ccg gag gcc ctt        241
Asp Phe Leu Thr Glu Trp Arg Arg Val Ser Lys Ala Pro Glu Ala Leu
             65                  70                  75 ttc ttt gtg caa ttt gag aag gga gag agc tac ttc cac atg cac gtg        289
Phe Phe Val Gln Phe Glu Lys Gly Glu Ser Tyr Phe His Met His Val
         80                  85                  90 ctc gtg gaa acc acc ggg gtg aaa tcc atg gtt ttg gga cgt ttc ctg        337
Leu Val Glu Thr Thr Gly Val Lys Ser Met Val Leu Gly Arg Phe Leu
     95                 100                 105 agt cag att cgc gaa aaa ctg att cag aga att tac cgc ggg atc gag        385
Ser Gln Ile Arg Glu Lys Leu Ile Gln Arg Ile Tyr Arg Gly Ile Glu
110                 115                 120                 125 ccg act ttg cca aac tgg ttc gcg gtc aca aag acc aga aat ggc gcc        433
Pro Thr Leu Pro Asn Trp Phe Ala Val Thr Lys Thr Arg Asn Gly Ala
                130                 135                 140 gga ggc ggg aac aag gtg gtg gat gag tgc tac atc ccc aat tac ttg        481
Gly Gly Gly Asn Lys Val Val Asp Glu Cys Tyr Ile Pro Asn Tyr Leu
            145                 150                 155 ctc ccc aaa acc cag cct gag ctc cag tgg gcg tgg act aat atg gaa        529
Leu Pro Lys Thr Gln Pro Glu Leu Gln Trp Ala Trp Thr Asn Met Glu
        160                 165                 170 cag tat tta agc gcc tgt ttg aat ctc acg gag cgt aaa cgg ttg gtg        577
Gln Tyr Leu Ser Ala Cys Leu Asn Leu Thr Glu Arg Lys Arg Leu Val
    175                 180                 185 gcg cag cat ctg acg cac gtg tcg cag acg cag gag cag aac aaa gag        625
Ala Gln His Leu Thr His Val Ser Gln Thr Gln Glu Gln Asn Lys Glu
190                 195                 200                 205 aat cag aat ccc aat tct gat gcg ccg gtg atc aga tca aaa act tca        673
Asn Gln Asn Pro Asn Ser Asp Ala Pro Val Ile Arg Ser Lys Thr Ser
                210                 215                 220
```

|   |   |
|---|---|
| gcc agg tac atg gag ctg gtc ggg tgg ctc gtg gac aag ggg att acc<br>Ala Arg Tyr Met Glu Leu Val Gly Trp Leu Val Asp Lys Gly Ile Thr<br>225 230 235 | 721 |
| tcg gag aag cag tgg atc cag gag gac cag gcc tca tac atc tcc ttc<br>Ser Glu Lys Gln Trp Ile Gln Glu Asp Gln Ala Ser Tyr Ile Ser Phe<br>240 245 250 | 769 |
| aat gcg gcc tcc aac tcg cgg tcc caa atc aag gct gcc ttg gac aat<br>Asn Ala Ala Ser Asn Ser Arg Ser Gln Ile Lys Ala Ala Leu Asp Asn<br>255 260 265 | 817 |
| gcg gga aag att atg agc ctg act aaa acc gcc ccc gac tac ctg gtg<br>Ala Gly Lys Ile Met Ser Leu Thr Lys Thr Ala Pro Asp Tyr Leu Val<br>270 275 280 285 | 865 |
| ggc cag cag ccc gtg gag gac att tcc agc aat cgg att tat aaa att<br>Gly Gln Gln Pro Val Glu Asp Ile Ser Ser Asn Arg Ile Tyr Lys Ile<br>290 295 300 | 913 |
| ttg gaa cta aac ggg tac gat ccc caa tat gcg gct tcc gtc ttt ctg<br>Leu Glu Leu Asn Gly Tyr Asp Pro Gln Tyr Ala Ala Ser Val Phe Leu<br>305 310 315 | 961 |
| gga tgg gcc acg aaa aag ttc ggc aag agg aac acc atc tgg ctg ttt<br>Gly Trp Ala Thr Lys Lys Phe Gly Lys Arg Asn Thr Ile Trp Leu Phe<br>320 325 330 | 1009 |
| ggg cct gca act acc ggg aag acc aac atc gcg gag gcc ata gcc cac<br>Gly Pro Ala Thr Thr Gly Lys Thr Asn Ile Ala Glu Ala Ile Ala His<br>335 340 345 | 1057 |
| act gtg ccc ttc tac ggg tgc gta aac tgg acc aat gag aac ttt ccc<br>Thr Val Pro Phe Tyr Gly Cys Val Asn Trp Thr Asn Glu Asn Phe Pro<br>350 355 360 365 | 1105 |
| ttc aac gac tgt gtc gac aag atg gtg atc tgg tgg gag gag ggg aag<br>Phe Asn Asp Cys Val Asp Lys Met Val Ile Trp Trp Glu Glu Gly Lys<br>370 375 380 | 1153 |
| atg acc gcc aag gtc gtg gag tcg gcc aaa gcc att ctc gga gga agc<br>Met Thr Ala Lys Val Val Glu Ser Ala Lys Ala Ile Leu Gly Gly Ser<br>385 390 395 | 1201 |
| aag gtg cgc gtg gac cag aaa tgc aag tcc tcg gcc cag ata gac ccg<br>Lys Val Arg Val Asp Gln Lys Cys Lys Ser Ser Ala Gln Ile Asp Pro<br>400 405 410 | 1249 |
| act ccc gtg atc gtc acc tcc aac acc aac atg tgc gcc gtg att gac<br>Thr Pro Val Ile Val Thr Ser Asn Thr Asn Met Cys Ala Val Ile Asp<br>415 420 425 | 1297 |
| ggg aac tca acg acc ttc gaa cac cag cag ccg ttg caa gac cgg atg<br>Gly Asn Ser Thr Thr Phe Glu His Gln Gln Pro Leu Gln Asp Arg Met<br>430 435 440 445 | 1345 |
| ttc aaa ttt gaa ctc acc cgc cgt ctg gat cat gac ttt ggg aag gtc<br>Phe Lys Phe Glu Leu Thr Arg Arg Leu Asp His Asp Phe Gly Lys Val<br>450 455 460 | 1393 |
| acc aag cag gaa gtc aaa gac ttt ttc cgg tgg gca aag gat cac gtg<br>Thr Lys Gln Glu Val Lys Asp Phe Phe Arg Trp Ala Lys Asp His Val<br>465 470 475 | 1441 |
| gtt gag gtg gag cat gaa ttc tac gtc aaa aag ggt gga gcc aag aaa<br>Val Glu Val Glu His Glu Phe Tyr Val Lys Lys Gly Gly Ala Lys Lys<br>480 485 490 | 1489 |
| aga ccc gcc ccc agt gac gca gat ata agt gag ccc aaa cgg gtg cgc<br>Arg Pro Ala Pro Ser Asp Ala Asp Ile Ser Glu Pro Lys Arg Val Arg<br>495 500 505 | 1537 |
| gag tca gtt gcg cag cca tcg acg tca gac gcg gaa gct tcg atc aac<br>Glu Ser Val Ala Gln Pro Ser Thr Ser Asp Ala Glu Ala Ser Ile Asn<br>510 515 520 525 | 1585 |
| tac gca gac agg tac caa aac aaa tgt tct cgt cac gtg ggc atg aat<br>Tyr Ala Asp Arg Tyr Gln Asn Lys Cys Ser Arg His Val Gly Met Asn<br>530 535 540 | 1633 |

```
ctg atg ctg ttt ccc tgc aga caa tgc gag aga atg aat cag aat tca    1681
Leu Met Leu Phe Pro Cys Arg Gln Cys Glu Arg Met Asn Gln Asn Ser
        545                 550                 555 aat atc tgc ttc act cac gga cag aaa gac tgt tta gag tgc ttt ccc    1729
Asn Ile Cys Phe Thr His Gly Gln Lys Asp Cys Leu Glu Cys Phe Pro
        560                 565                 570 gtg tca gaa tct caa ccc gtt tct gtc gtc aaa aag gcg tat cag aaa    1777
Val Ser Glu Ser Gln Pro Val Ser Val Val Lys Lys Ala Tyr Gln Lys
575                 580                 585 ctg tgc tac att cat cat atc atg gga aag gtg cca gac gct tgc act    1825
Leu Cys Tyr Ile His His Ile Met Gly Lys Val Pro Asp Ala Cys Thr
590                 595                 600                 605 gcc tgc gat ctg gtc aat gtg gat ttg gat gac tgc atc ttt gaa caa    1873
Ala Cys Asp Leu Val Asn Val Asp Leu Asp Asp Cys Ile Phe Glu Gln
                610                 615                 620 taa                                                                1876

<210> SEQ ID NO 3
<211> LENGTH: 621
<212> TYPE: PRT
<213> ORGANISM: adeno-associated virus 2

<400> SEQUENCE: 3

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255
```

```
Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620
```

USE OF AAV REPLICATION MACHINERY FOR IMPROVED PROTEIN PRODUCTION

FIELD OF THE INVENTION

This invention relates to the fields of nucleic acid constructs and cell lines that allow for the increased expression of endogenous or heterologous target protein.

BACKGROUND OF THE INVENTION

Industrial production of recombinant proteins covers a wide area of developments and applications. The yield of recombinant protein per cell or per L of culture medium is an important asset for the development of improved production systems.

Current methods of expressing genes in mammalian or insect cells for the industrial production of recombinant proteins, monoclonals or vaccines include the use of stable cell lines or the transfection of producer cells using vectors, such as those which are derived from adenoviruses, sindbis viruses, or baculoviruses. Other methods for introduction of an exogenous gene in a mammalian cell or insect cell include direct injection of DNA, the use of ligand-DNA conjugates, the use of adenovirus-ligand-DNA conjugates, calcium phosphate precipitation, and methods which utilize a liposome- or polycation-DNA complex.

In nature, baculoviruses are double-stranded DNA-containing viruses that infect a variety of different insect species. The family of baculoviruses can be divided in two genera, one of which are the nucleopolyhedroviruses. The nucleopolyhedroviruses induce the formation of paracrystalline occlusion bodies in the nuclei of infected host cells. These occlusion bodies are composed primarily of a single viral protein, polyhedrin, which is expressed at very high levels. The polyhedrin gene has been cloned and sequenced and its unique features have provided the basis for the development of a series of baculovirus expression vectors (Summers, M. D. and Smith, G. E., TAES Bull. 1555 (1987); Luckow, V. A. and Summers, M. D., Biotechnology 6:47-55 (1988); Miller, L. K., Ann. Rev. Microbiol. 42:177-179 (1988); U.S. Pat. No. 4,745,051, G. E. Smith and M. D. Summers (Filed May 27, 1983; Issued May 17, 1988)).

The baculovirus-expression system used in conjunction with insect cells has become well-established for the production of proteins, due to its advantages in versatility and speed. In the baculovirus-expression system, a recombinant baculoviral vector is used to introduce a gene of interest into insect cells. Infection of the insect cells results in replication of the recombinant baculovirus vector genome, thereby increasing the number of genetic templates that encode the gene of interest and increasing the level of recombinant protein expression.

Baculovirus-mediated protein expression provides correct folding of recombinant proteins as well as disulfide-bond formation, oligomerization and other important post-translational modifications that provide proper biological activity and function. Indeed, protein folding and post-translational processing of an eukaryotic protein in insect-cells is quite comparable to mammalian cell lines. Furthermore, insect cells can be grown on serum free media which is an advantage in terms of costs as well as of biosafety. Another advantage of baculovirus-mediated protein expression is that baculoviruses only infect Lepidopteran insects, thereby being noninfectious for vertebrates and relatively safe genetic manipulation agents. In addition, the baculovirus-expression system is known to be a technology platform that results in high protein expression levels in insect cells. A disadvantage of the baculovirus expression system is that infection of the producer cell (insect cell) is lethal to that cell within a few days hampering continuous production of the recombinant protein of interest.

Zeng et al. (2007, Stem Cells 25: 1055-1061) disclose a baculovirus expression construct comprising a gene of interest as well as an AAV rep78/68 gene and AAV ITR sequences for integration of the construct into the AAVS1 site in the human genome of human embryonic stem cells.

Sollerbrant et al. (2001, J. Gen. Virol. 82: 2051-2060) disclose mammalian HEK293 cells transfected with separate baculovirus constructs comprising (i) a reporter gene flanked by AAV ITR sequences, (ii) an AAV rep gene, and (iii) an AAV cap gene, respectively, for production of rAAV vectors.

There is however, still a need in the art for increased production levels of gene products of interest in cells such as insect cells.

DESCRIPTION OF THE INVENTION

Definitions

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

The terms "substantially identical", "substantial identity" or "essentially similar" or "essential similarity" means that two peptide or two nucleotide sequences, when optimally aligned, such as by the programs GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively percent similarity or identity may be determined by searching against databases such as FASTA, BLAST, etc.

Nucleotide sequences encoding AAV Rep proteins of the invention may also be defined by their capability to hybridize with the nucleotide sequence of SEQ ID NO. 2, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridize at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e. at least for 10 hours and preferably washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridize at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

The terms "transformed" or "transfected" are used interchangeably and refer to the process by which exogenous DNA or RNA is transferred or introduced into an appropriate host cell. Additionally, nucleic acids encoding other heterologous proteins may be introduced into the host cell. Such transfected cells include stably transfected cells wherein the inserted DNA is rendered capable of replication in the host cell. Typically, stable transfection requires that the exogenous DNA be transferred along with a selectable marker nucleic acid sequence, such as for example, a nucleic acid sequence that confers antibiotic resistance, which enables the selection of the stable transfectants. This marker nucleic acid sequence may be ligated to the exogenous DNA or be provided independently by simultaneous cotransfection along with the exogenous DNA. Transfected cells also include transiently expressing cells that are capable of expressing the RNA or DNA for limited periods of time. The transfection procedure depends on the host cell being transfected. It can include packaging the polynucleotide in a virus as well as direct uptake of the polynucleotide. Transformation can result in incorporation of the inserted DNA into the genome of the host cell or the maintenance of the inserted DNA within the host cell in plasmid form. Methods of transformation/transfection are well known in the art and include, but are not limited to, direct injection, such as microinjection, viral infection, particularly replication-deficient adenovirus infection, electroporation, lipofection, calcium phosphate-mediated direct uptake and the like.

DETAILED DESCRIPTION OF THE INVENTION

The present invention relates to a method of using the AAV replication machinery for enhanced production of a protein and/or a nucleic acid sequence of interest in a cell. Co-expression of one or more AAV Rep proteins and a nucleic acid sequence flanked by AAV-ITRs increases both the expression of the protein of interest and the number of transcribed copies of the nucleic acid sequence of interest.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus *Dependovirus*. As may be deduced from the name of their genus, members of the *Dependovirus* are unique in that they usually require coinfection with a helper virus such as adenovirus or herpes virus for productive infection in cell culture. The genus *Dependovirus* includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wtAAV infection in mammalian cells the Rep genes (i.e. Rep78 and Rep52) are expressed from the P5 promoter and the P19 promoter, respectively and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

A "recombinant parvoviral or AAV vector" (or "rAAV vector") herein refers to a vector comprising one or more polynucleotide sequences of interest, genes of interest or "transgenes" that are flanked by parvoviral or AAV inverted terminal repeat sequences (ITRs). Such rAAV vectors can be replicated and packaged into infectious viral particles when present in an insect host cell that is expressing AAV rep and cap gene products (i.e. AAV Rep and Cap proteins). When an rAAV vector is incorporated into a larger nucleic acid construct (e.g. in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions.

In a first aspect, the present invention relates to a method for producing a gene product of interest, the method comprising the steps of:
a) providing a cell comprising:
 i) a first expression cassette comprising a nucleotide sequence encoding the gene product of interest which is operably linked to a promoter capable of driving expression of the gene product in the cell, and wherein the first expression cassette is flanked by at least one parvoviral inverted terminal repeat (ITR) nucleotide sequence;
 ii) at least a second expression cassette comprising a nucleotide sequence encoding at least one parvoviral Rep protein which is operably linked to a promoter capable of driving expression of the Rep proteins in the cell;
b) culturing the cell defined in a) under a condition conducive to the expression of the first and second expression cassettes; and,
c) optionally recovery of the gene product of interest.

A gene product of interest of the invention may be a polypeptide of interest or a nucleotide (nucleic acid) sequence of interest. A polypeptide may be of any length including a dipeptide, a tripeptide, an (oligo) peptide, a polypeptide or a protein. It is understood that the terms peptide, polypeptide and protein may be used interchangeably herein. The polypeptide may be a homologous polypeptide, but in a preferred embodiment of the invention the polypeptide is a heterologous polypeptide to the host cell.

A nucleotide (nucleic acid) sequence according to the invention may be present in the form of RNA or in the form of DNA including genomic DNA, i.e. DNA including the introns, cDNA or synthetic DNA and mixed DNA-RNA sequences.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically be operably linked to another promoter sequence or, if applicable, another secretory signal sequence and/or terminator sequence than in its natural environment.

The term "heterologous" when used with respect to a nucleic acid or polypeptide molecule refers to a nucleic acid or polypeptide from a foreign cell which does not occur naturally as part of the organism, cell, genome or DNA or RNA sequence in which it is present, or which is found in a cell or location or locations in the genome or DNA or RNA sequence that differ from that in which it is found in nature. Heterologous nucleic acids or proteins are not endogenous to the cell into which they are introduced, but have been obtained from another cell or synthetically or recombinantly produced. Generally, though not necessarily, such nucleic acids encode proteins that are not normally produced by the cell in which the DNA is transcribed or expressed, similarly exogenous RNA codes for proteins not normally expressed in the cell in which the exogenous RNA is present. Furthermore, it is known that a heterologous protein or polypeptide can be composed of homologous elements arranged in an order and/or orientation not normally found in the host organism, tissue or cell thereof in which it is transferred, i.e. the nucleotide sequence encoding said protein or polypeptide originates from the same species but is substantially modified from its native form in composition and/or genomic locus by deliberate human intervention. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

The polypeptide of interest may have industrial or medicinal (pharmaceutical) applications. Examples of proteins or polypeptides with industrial applications include enzymes such as e.g. lipases (e.g. used in the detergent industry), proteases (used inter alia in the detergent industry, in brewing and the like), cell wall degrading enzymes (such as, cellulases, pectinases, beta.-1,3/4- and beta.-1,6-glucanases, rhamnogalacturonases, mannanases, xylanases, pullulanases, galactanases, esterases and the like, used in fruit processing wine making and the like or in feed), phytases, phospholipases, glycosidases (such as amylases, beta.-glucosidases, arabinofuranosidases, rhamnosidases, apiosidases and the like), dairy enzymes (e.g. chymosin). Mammalian, and preferably human, polypeptides with therapeutic, cosmetic or diagnostic applications include, but are not limited to, enzymes (for enzyme replacement therapy), hormones, chymokines, interleukins, (humanised) monoclonal antibodies, and the like. Examples include, but are not limited to, insulin, apolipoprotein A (preferably apolipoprotein A1) or E, serum albumin (HSA), CFTR, Factor IX, lactoferrin, lipoprotein lipase (LPL, preferably LPL S447X; see 01/00220), hemoglobin α and β, tissue plasminogen activator (tPA), erythropoietin (EPO), tumor necrosis factors (TNF), BMP (Bone Morphogenic Protein), growth factors (G-CSF, GM-CSF, M-CSF, PDGF, EGF, IGF, and the like), peptide hormones (e.g. calcitonin, somatomedin, somatotropin, growth hormones, follicle stimulating hormone (FSH), cytokines or interleukins (IL-x), interferons (IFN-y), insulin receptor, EGF receptor, tyrosine hydroxylase, glucocerebrosidase, Uridine Diphosphate Glucuronosyltransferase (UGT), Retinitis Pigmentose GTPase Regulator Interacting Protein (RP-GRIP), porphobilinogen deaminase (PBGD) and alanine:glyoxylate aminotransferase. Included are furthermore single chain variable antibody fragments (scFv). Also included are protozoic, bacterial and viral antigens, e.g. for use as vaccines, including e.g. heat-labile toxin B-subunit, cholera toxin B-subunit, envelope surface protein Hepatitis B virus, capsid protein Norwalk virus, glycoprotein B Human cytomegalovirus, glycoprotein S, and transmissible gastroenteritis corona virusreceptors, human T-lymphotropic virus (HTLV-1) p40$^x$, HTLV-1 env, human immunodeficiency virus (HIV-1) gag, pol, sor, gp41, and gp120, adenovirus E1a, Japanese encephalitis virus env (N), bovine papilloma virus 1 (BPV1) E2, HPV6b E2, BPV1 E6, hepatitis B surface antigen, HIV-1 env, HIV-1 gag, HTLV-1 p40.sup.x, $D.$ $melanogaster$ Kruppel gene product, bluetongue virus VP2 and VP3, human parainfluenza virus hemagglutinin (HA), influenza polymerases PA, PB1, and PB2, influenza virus HA, lymphocytic choriomeningitis virus (LCMV) GPC and N proteins, $Neurospora$ $crassa$ activator protein, polyomavirus T antigen, simian virus 40 (SV40) small t antigen, SV40 large T antigen, Punta Toro phlebovirus N and Ns proteins, simian rotavirus VP6, CD4 (T4), Hantaan virus structural protein, human B lymphotrophic virus 130-kd protein, hepatitis A virus, VP1, VP1 and VP2 of Human parvovirus-B19, non-Parvoviral Cap proteins, Classical Swine Fever Virus E2-glycoprotein and the like. Further included mutants or analogues of the said polypeptides.

A nucleotide sequence encoding a heterologous protein may be derived in whole or in part from any source known to the art, including a bacterial or viral genome or episome, eukaryotic nuclear or plasmid DNA, cDNA or chemically synthesised DNA. The nucleotide sequence encoding a protein of interest may constitute an uninterrupted coding region or it may include one or more introns bounded by appropriate splice junctions, it may further be composed of segments derived from different sources, naturally occurring or synthetic. The nucleic acid sequence encoding the protein of interest according to the method of the invention, is preferably a full-length nucleotide sequence, but may also be a functionally active part or other part of said full-length nucleotide sequence.

In a preferred embodiment, the nucleotide sequences of interest may encode any polypeptide, but preferably a polypeptide having industrial or medicinal (pharmaceutical) applications. Examples of polypeptides having industrial or medicinal applications are provided above.

Alternatively or in combination with previous preferred embodiments, in a further preferred embodiment, a cell for use in the method of the invention may be an insect cell or a mammalian cell. In a preferred embodiment any insect cell or mammalian cell, which allows for expression of the gene product according to the method of the invention and which can be maintained in culture, can be used in accordance with the present invention. In another preferred embodiment the insect cell or mammalian cell is a cell susceptible to infection by baculovirus or a cell that allows replication of baculovirus. In a further preferred embodiment the cell is an insect cell. For example, the cell line used can be from $Spodoptera$ $frugiperda,$ $drosophila$ cell lines, or mosquito cell lines, e.g., $Aedes$ $albopictus$ derived cell lines.

Preferred insect cells or cell lines for use in the present invention, include e.g. Se301, SeIZD2109, SeUCR1, Sf9, Sf900+, Sf21, S2, BTI-TN-5B1-4, MG-1, Tn368, HzAm1, Ha2302, Hz2E5, High Five (Invitrogen, CA, USA) and expresSF+® (U.S. Pat. No. 6,103,526; Protein Sciences Corp., CT, USA).

Preferred mammalian cells or cell lines for use in the present invention, include e.g. HeLa, Vero, Per.C6, Hek293, CHO, MDCK, CEK, hybridoma, and nonsecreting (NS0) myeloma cell lines. In one embodiment, a cell for use in the method of the invention is not a human embryonic stem cell. In another embodiment, a cell for use in the method of the invention is not an embryonic stem cell.

The term "first expression cassette" is herein defined as a nucleic acid construct comprising a nucleotide sequence encoding the gene product of interest which is operably linked to a promoter capable of driving expression of the gene product in the cell, and wherein the first expression cassette is flanked by at least one parvoviral inverted terminal repeat (ITR) nucleotide sequence. The first expression cassette optionally comprises other expression control sequences operably linked to the gene product of interest.

Alternatively or in combination with previous preferred embodiments, in a further preferred embodiment, the first expression cassette of the invention is flanked by at least two parvoviral ITR nucleotide sequences. In a more preferred embodiment, the first expression cassette is flanked on either side, i.e., both the 3' end and the 5' end, by parvoviral ITR nucleotide sequences. The term "flanked" is understood herein as the ITRs being close enough to the first expression cassette to allow for replication, i.e. increase in copynumber, of the first expression cassette by the at least one Parvoviral Rep protein. Preferably, the distance between a flanking ITR sequence and the most upstream or downstream (i.e. terminal) regulatory element in the expression cassette is less than 50, 20, 10, 5, 2, 1, 0.5, 0.2 or 0.1 kb, more preferably the distance is less than 50, 20 or 10 nucleotides, and most preferably the flanking ITR is directly linked to the expression cassette.

The term "second expression cassette" is herein defined as a nucleic acid construct comprising a nucleotide sequence encoding at least one parvoviral replication (Rep) protein which is operably linked to a promoter capable of driving expression of the Rep protein in the cell. The second expression cassette optionally comprises other expression control sequences operably linked to the at least one parvoviral Rep protein.

In the method of the invention, the at least one parvoviral Rep protein encoded in the second expression cassette, preferably at least is an AAV Rep 78 and/or a Rep 68 protein, or a corresponding Rep protein from another Parvovirus. The second expression cassette may comprise an open reading frame comprising nucleotide sequences encoding parvoviral Rep proteins, wherein the initiation codon for translation of the parvoviral Rep78 protein is an initiation codon that effects partial exon skipping upon expression in the cell. However, because the Rep 52 and Rep 40 proteins are not necessary for ITR-mediated replication their expression and presence is not required. Hence, embodiments wherein, the cell comprises a second expression cassette for a parvoviral Rep78 or Rep68 protein and a third expression cassette for a Rep52 or Rep40 parvoviral protein are not excluded from the invention but the presence of such a third expression cassette is not required, and its absence is preferred.

Preferably in the method of the invention, the parvoviral ITR sequences and parvoviral Rep protein are from an adeno-associated virus (AAV). An "AAV-ITR" sequence or an "AAV Rep protein" used in the context of the present invention is "substantially identical" to an AAV-ITR or an AAV Rep protein. Such "substantially identical" sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR sequence or nucleotide sequence encoding at least one Rep protein. More preferably, the AAV-ITR comprises a sequence which is substantially identical to SEQ ID NO:1. Even more preferably, the AAV-ITR comprises a sequence which is identical to SEQ ID NO:1.

In a preferred embodiment, the nucleotide sequence encodes at least one parvoviral Rep protein that is substantially identical to SEQ ID NO:3. Even more preferably, the parvoviral Rep protein encoded by the amino acid sequence of the second expression cassette is identical to SEQ ID NO:3.

A nucleotide sequence encoding at least one parvoviral Rep protein, is herein understood as a nucleotide sequence encoding one or more non-structural Rep proteins. Preferably the nucleotide sequence encodes at least the AAV Rep78, or the Rep78 and Rep68 proteins, that are required and sufficient for replication of the first expression cassette flanked by ITRs, and expression of the gene product of interest in the cell. The nucleic acid sequence preferably is from an AAV which normally infects humans (e.g., serotypes 1, 2, 3A, 3B, 4, 5, and 6) or primates (e.g., serotypes 1 and 4). An example of a nucleic acid sequence encoding AAV Rep proteins is given in SEQ ID No 2, which depicts a part of the AAV serotype-2 sequence genome encoding the Rep proteins. The Rep78 coding sequence comprises nucleotides 11-1876 and the Rep52 coding sequence comprises nucleotides 683-1876. It is understood that the exact molecular weights of the Rep78 and Rep52 proteins, as well as the exact positions of the translation initiation codons may differ between different parvoviruses. However, the skilled person will know how to identify the corresponding position in nucleotide sequence from other parvoviruses than AAV-2.

Alternatively or in combination with previous preferred embodiments, in a further preferred embodiment, one or more of the expression cassettes of the invention are part of an expression vector. In another preferred embodiment the first expression cassette and the second expression cassette are part of a single expression vector and preferably flanked by at least one Parvoviral ITR nucleotide sequence. In still another preferred embodiment, the first expression cassette and the second expression cassette are part of two separate expression vectors. The term "vector" as used herein refers to a nucleic acid compound used for introducing exogenous DNA into host cells. The vector may be a vector for integration into the genome of the host cell (used in the method of the invention) or the vector may be a vector that does not integrate into the host cell's genome such as e.g. an episomal vector. An example of an episomal vector is e.g. a plasmid vector thus at least comprises a replicon and a DNA segment that may be used for insertion of the exogenous DNA into the vector by recombinant techniques, preferably without interfering with the plasmids capability to replicate. The replicon preferably is a replicon for replication in the cell used in the method of the invention. Vectors usually comprise further genetic elements to facilitate their use in molecular cloning, such as e.g. selectable markers, multiple cloning sites and the like (see below). An "expression vector" as used herein refers to any plasmid-based cloning vector, in which a promoter and other regulatory elements are present to enable transcription of inserted exogenous DNA when the expression vector is present in a suitable host cell. A "shuttle vector" refers to a plasmid vector that is capable of replication and stable maintenance in at least two different host organisms, e.g. two organisms of different species or different genera. For this capability the shuttle vector may rely on a single broad host-range replicon but usually a shuttle vector will comprise different replicons for different host-organisms or different groups of host-organisms.

In one embodiment of the invention, the first expression cassette, comprising the gene of interest and at least one ITR, does not integrate into the (host) cell's genome. Preferably, at least the first expression cassette is present on a vector that does not integrate into the (host) cell's genome, e.g. an episomal vector. The second expression cassette may be present on the same non-integrating vector as the first cassette, on a different episomal vector or the second expression cassette may integrate into the host cell's genome.

In a preferred embodiment an expression vector comprises a multiple cloning site, as is known in the art. Such a multiple cloning site contains several different unique restriction sites that may conveniently be used for insertion of fragments into the vectors.

In a preferred embodiment, the first expression cassette and/or the second expression cassette comprises at least a promoter that is active in the cell. When the cell is an insect cell, techniques known to one skilled in the art for expressing foreign genes in insect host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W. H. Freeman and Richardson, C. D., 1995, Baculovirus Expression Protocols, Methods in Molecular Biology, volume 39; U.S. Pat. No. 4,745,051; US2003148506; and WO 03/074714. In a preferred embodiment at least one of the expression cassettes is comprised in a baculoviral vector. In another embodiment, a particularly suitable promoter for transcription of the nucleotide sequence of the invention encoding of the AAV Rep proteins is e.g. the polyhedron promoter. However, other promoters that are active in insect cells are known in the art, e.g. the p10, p35, IE-1 or ΔIE-1 promoters and further promoters described in the above references.

When the cell is a mammalian cell, the nucleotide sequence encoding a gene product of interest, preferably is operably linked to a mammalian cell-compatible expression control sequence, e.g., a promoter. Many such promoters are known in the art (see Sambrook and Russel, 2001, supra). Constitutive promoters that are broadly expressed in many cell-types, such as the CMV promoter may be used. However, more preferred will be promoters that are inducible, tissue-specific, cell-type-specific, or cell cycle-specific. For example, for liver-specific expression a promoter may be selected from an α1-anti-trypsin promoter, a thyroid hormone-binding globulin promoter, an albumin promoter, LPS (thyroxine-binding globlin) promoter, HCR-ApoCII hybrid promoter, HCR-hAAT hybrid promoter and an apolipoprotein E promoter. Other examples include the E2F promoter for tumor-selective, and, in particular, neurological cell tumor-selective expression (Parr et al., 1997, Nat. Med. 3:1145-9) or the IL-2 promoter for use in mononuclear blood cells (Hagenbaugh et al., 1997, J Exp Med; 185: 2101-10). Preferred promoters for expression in mammalian cells are mammalian viral promoters, such as CMVie, SV40, RSV, MMTV-LTR and LTR; constitutive cellular promoters, such as beta-actin, elongation factor 1, early growth response 1, ferritine, HSP70 and GAPDH; and tissue specific promoters, such as AAT, alpha-actin, CMD1, NSE, creatine-kinase, MLC-2v and EAlb/hAAT.

Preferably the expression vector is compatible with the cell in which the present invention is carried out. The person skilled in the art will know how to select an appropriate expression vector.

An "insect cell-compatible expression vector" is understood to be a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cell's genome but the presence of the vector in the insect cell need not be permanent and transient and/or episomal vectors are also included. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

A wide variety of vectors compatible with mammalian cells is available to the skilled person (see e.g. Sambrook and Russel, 2001, supra). The vector may integrate into the mammalian cells genome but the presence of the vector in the mammalian cell need not be permanent and transient and/or episomal vectors are also included. The vectors can be introduced by any means known e.g. $CaPO_4$-transfection, lipofection, transfection or electroporation. In a preferred embodiment, the vector is an adenovirus, an adeno-associated virus, or a baculovirus. In a more preferred embodiment, the vector is an adenovirus, i.e. the construct is an adenoviral vector. Adenoviral vectors and methods for their use are described in X Danthinne and M J Imperiale (2000) Production of first generation adenoviral vectors: a review, Gene Therapy 7(20): 1707-1714.

Alternatively or in combination with previous preferred embodiments, in a further preferred embodiment, the second expression cassette may be transfected or transformed into a cell. Preferred methods for transfection or transformation of the second expression cassette are eg $CaPO_4$-transfection, lipofection, transfection and electroporation.

Alternatively or in combination with previous preferred embodiments, in a further preferred embodiment, the first expression cassette and/or the second expression cassette and/or the expression vector is introduced into the cell by transfection (or transformation). In a more preferred embodiment the transfection is a viral transfection, a chemical transfection or electroporation. In an more preferred embodiment the transfection is used to generate a stable cell line. In an even more preferred embodiment, the transfection for generation of a stable cell line is $CaPO_4$ transfection, lipofection or electroporation. Transfection (or transformation) of the expression vector and the nucleic acid construct may be carried out either one after the other or as a cotransfection. In a preferred embodiment, the second expression cassette is transfected to generate a stable cell line capable of expression at least one parvoviral Rep protein.

Alternatively or in combination with previous preferred embodiments, in a further preferred embodiment, the production of the gene product of interest is enhanced when compared to production under the same conditions, however without the at least one Parvoviral ITR nucleotide sequence and/or the at least one Parvoviral Rep protein present. This may be measured by RT-QPCR assay and or protein quantitative assays (eg ELISA etc.). The skilled person will know how to determine the production of the gene product of interest using these or other methods known in the art.

Optionally the method of the invention may comprise recovery, or isolation and/or purification, of the polypeptide. The polypeptide may e.g. be recovered from the culture medium by standard protein purification techniques, including a variety of chromatography methods known in the art per se. Collecting the polypeptide of interest depends on the expressed polypeptide and the host cells used but can comprise recovering the polypeptide through isolation. When applied to a polypeptide, the term "isolation" indicates that the protein is found in a condition other than its native environment. In a preferred form, the isolated polypeptide is substantially free of other proteins/polypeptides, particularly other homologous polypeptides. It is preferred to provide the polypeptide in a greater than 40% pure form, more preferably greater than 60% pure form. Even more preferably it is preferred to provide the polypeptide in a highly purified form, i.e., greater than 80% pure, more preferably greater than 95% pure, and even more preferably greater than 99% pure, as determined by SDS-PAGE. It can be very helpful to express the polypeptide of interest as a fusion polypeptide to facilitate polypeptide purification and polypeptide detection on for instance Western blot and in an ELISA. Suitable fusion sequences include, but are not limited to, the sequences of proteins such as for instance glutathione-S-transferase, maltose-binding protein, metal-binding polyhistidine, green fluorescent protein, luciferase and β-galactosidase. The polypeptide may also be coupled to non-peptide carriers, tags or labels that facilitate tracing of the polypeptide, both in vivo and in vitro, and allow for the identification and quantification of binding of the polypeptide to substrates. Such labels, tags or carriers are well-known in the art and include, but are not limited to, biotin, radioactive labels and fluorescent labels.

Alternatively or in combination with previous preferred embodiments, in a further preferred embodiment, the cell does not comprise at least one of a Parvoviral Cap protein and a nucleotide sequence encoding a Parvoviral Cap protein.

Alternatively or in combination with previous preferred embodiments, in a further preferred embodiment of the method of the invention, the AAV vector genome copy number increases at least 2-fold, more preferably at least 5-fold, more preferably at least 10-fold, more preferably at least 20-fold, more preferably at least 50-fold, more preferably at least 100-fold, more preferably at least 150-fold, more preferably at least 200-fold, as compared to the method wherein the cell is not provided with a nucleotide sequence encoding at least one parvoviral Rep protein which is operably linked to a promoter capable of driving expression of the Rep proteins in the cell. The person skilled in the art knows how to determine a copy number, e.g. an AAV vector genome copy number, e.g. by Q-PCR.

Alternatively or in combination with previous preferred embodiments, in a further preferred embodiment of the method of the invention, the amount of protein expression of the gene product of interest increases at least 1.5-fold, more preferably at least 2-fold, more preferably at least 5-fold, more preferably at least 10-fold, more preferably at least 15-fold, more preferably at least 20-fold, more preferably at least 25-fold, more preferably at least 30-fold, as compared to the method wherein the cell is not provided with a nucleotide sequence encoding at least one parvoviral Rep protein which is operably linked to a promoter capable of driving expression of the Rep proteins in the cell. The person skilled in the art will know how to determine the amount of protein expression of the gene product of interest, e.g. by ELISA or Western blot.

Alternatively or in combination with previous preferred embodiments, in a further preferred embodiment of the method of the invention, the activity of the protein encoded by the gene product of interest increases at least 1.5-fold, more preferably at least 2-fold, more preferably at least 5-fold, more preferably at least 10-fold, more preferably at least 15-fold, more preferably at least 20-fold, more preferably at least 25-fold, more preferably at least 30-fold, as compared to the method wherein the cell is not provided with a nucleotide sequence encoding at least one parvoviral Rep protein which is operably linked to a promoter capable of driving expression of the Rep proteins in the cell.

In a second aspect, the present invention relates to a cell as described above, wherein the cell does not comprise at least one of a Parvoviral Cap protein and a nucleotide sequence encoding a Parvoviral Cap protein.

Alternatively or in combination with previous preferred embodiments, in a further preferred embodiment, the cell does not express at least one of a Parvoviral Rep 52 protein and a Rep 40 protein, e.g. an AAV Rep 52 and Rep 40 protein, or a corresponding Parvoviral replication protein.

In a third aspect, the present invention relates to a cell as described above, wherein the cell does not express at least one of a Parvoviral Rep 52 protein and a Rep 40 protein, e.g. an AAV Rep 52 and Rep 40 protein, or a corresponding Parvoviral replication protein.

In a preferred embodiment the cell may be a cell line. In a more preferred embodiment the cell may be a stable cell line.

In a fourth aspect, the present invention relates to a non-human transgenic animal or a transgenic plant comprising a cell as described above.

Another aspect of the invention relates to a transgenic animal comprising in its somatic and germ cells a vector as defined above. The transgenic animal preferably is a non-human animal. Methods for generating transgenic animals are e.g. described in WO 01/57079 and in the references cited therein. Such transgenic animals may be used in a method for producing a polypeptide of interest, the method comprising the step of recovering a body fluid from a transgenic animal comprising the vector or a female descendant thereof, wherein the body fluid contains the polypeptide, and, optionally recovery of the polypeptide from the body fluid. Such methods are also described in WO 01/57079 and in the references cited therein. The body fluid containing the polypeptide preferably is blood or more preferably milk.

Yet another aspect of the invention relates to a transgenic plant comprising in its cells a vector as defined above. Methods for generating transgenic plants are e.g. described in U.S. Pat. No. 6,359,196 and in the references cited therein. Such transgenic plants may be used in a method for producing an polypeptide of interest, the method comprising the step of recovering a part of a transgenic plant comprising in its cells the vector or a part of a descendant of such transgenic plant, whereby the plant part contains the polypeptide, and, optionally recovery of the polypeptide from the plant part. Such methods are also described in U.S. Pat. No. 6,359,196 and in the references cited therein.

Although the methodology described herein is believed to contain sufficient detail to enable one skilled in the art to practice the present invention, the plasmids can be constructed and purified using standard recombinant DNA techniques described in T. Maniatis, E. F. Fritsch and J. Sambrook, Molecular Cloning: A Laboratory Manual, Cold Spring Harbor Laboratory (1982) under the current regulations described in United States Dept. of HEW, National Institute of Health (NIH) Guidelines for Recombinant DNA Research. These references include procedures for the following standard methods: cloning procedures with *E. coli* plasmids, transformation of *E. coli* cells, plasmid DNA purification, phenol extraction of DNA, ethanol precipitation of DNA, agarose gel electrophoresis, purification of DNA fragments from agarose gels, and restriction endonuclease and other DNA-modifying enzyme reactions.

Example 3 herein demonstrates an unexpected advantage of the present invention: co-infection of an insect cell with (1) a baculovirus harboring a transgene of interest with, (2) a baculovirus expressing a parvoviral (i.e. AAV) Rep protein, reduces cell death and increase the viable life-span of the co-infected insect cell. Thereby the production phase for the transgene of interest is prolonged and consequently the specific production yield is increased. Thus in a further aspect the invention relates to methods for reducing cell death and/or increasing viable life-span of insect cell infected with bacoluvirus and/or baculoviral vectors, wherein the method comprises the step of (co-)expressing a parvoviral Rep protein as herein defined above in the insect cell. Preferably, the Parvoviral replication protein is at least one of a Rep78 and a Rep68 protein. Preferably, the insect cell does not express at least one of a AAV Rep 52 protein and a Rep 40 protein or a corresponding Parvoviral replication protein.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Example 1

Enhanced Protein Expression in SF+ Cells by Co-Expression of the AAV-Rep Protein 1.1 Materials and Methods
1.1.1 Generation of Baculovirus Plasmids pVD142 and pVD143 were used to make recombinant baculoviruses. pVD142 contains the pCMV-p10-GFP expression cassette between ITRs and pVD143 contains the pPolH-AAV2 Rep78/ACG and the pCMV-p10-GFP expression cassette between ITRs. Recombinant Bac.VD142 and Bac.VD143 (p0) were generated with the flashBAC system. Subsequently, baculoviruses of p0 were amplified by diluting them 1:100 into log-phase grown SF+ cells at a density of 2E+6 cells/ml. Amplified baculoviruses of p1 were harvested three days after infection. Amplifying of next passages was performed in same manner.

1.1.2 Fluorometric Measurement in SF+ Cells

SF+ cells grown in log-phase and at a density of 2E+6 cells/ml were infected with baculovirus Bac.VD142 or Bac.VD143 (from passage p0 or p3) at a 1:100 dilution. Several different time points after infection GFP fluorescence was measured. First the amount of viable cells in each sample was determined using the Nucleocounter. Subsequently, the infected cells were diluted at a density of 0.5E+6 viable cells/ml with SF900II medium. Of each sample 100 µl (~50,000 cells) was transferred to a black 96-wells and fluorescence was measured using the Fluoroskan Ascent (excitation at 485 nm and extinction at 520 nm). When fluorescence was measured in cells resuspended in PBS (FIG. 2), 800 µl of cells (at a density of 0.5E+6 viable cells/ml) were centrifuged for 5 min at 1000 rcf. The cell pellet was resuspended in 800 µl PBS and fluorescence was measured as described above.

1.2 Results

Figure 1:
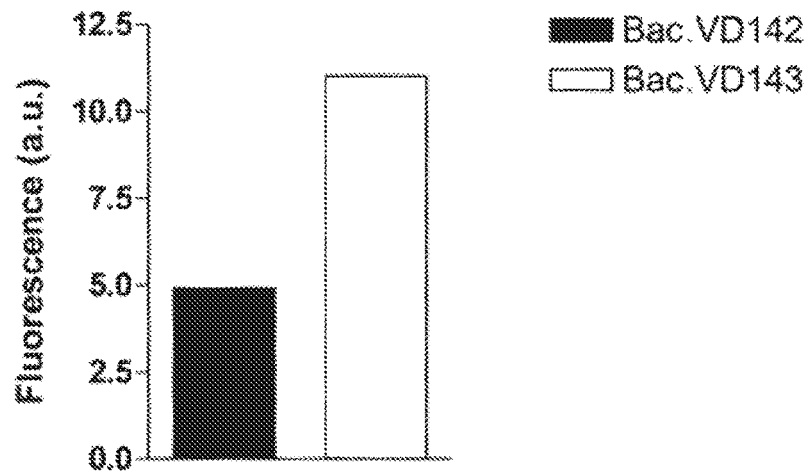
FIG. 1: GFP-fluorescence in SF900II medium three days after infection of SF+ cells with Bac.VD142 p0 or Bac.VD143 p0. Background fluorescence of the same amount of non-infected SF+ cells in medium was subtracted from the data.
Figure 2:
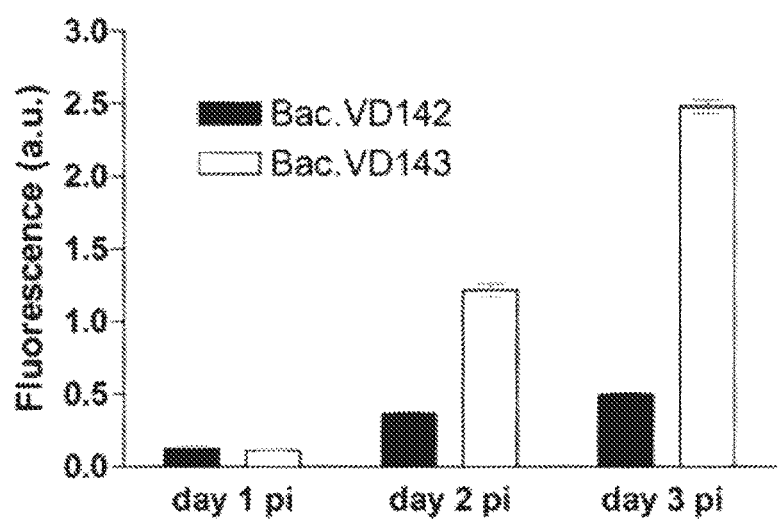
FIG. 2: GFP-fluorescence in living cells resuspended in PBS and measured at different times points post infection (pi) of SF+ cells with Bac.VD142 p3 or Bac.VD143 p3. Background fluorescence of the same amount of non-infected SF+ cells in PBS was subtracted from the data.

FIG. 1 shows fluorescence in living cells diluted in SF900II medium three days after infection of SF+ cells with Bac.VD142 p0 or Bac.VD143 p0, as measured using the Fluoroskan Ascent. Background fluorescence of the same amount of non-infected SF+ cells in medium was subtracted from the data. FIG. 2 shows fluorescence in living cells resuspended in PBS measured in duplo at different times points post infection (pi) of SF+ cells with Bac.VD142 p3 or Bac.VD143 p3. Enhanced GFP expression in SF+ cells infected with Bac.VD143 is evident. After three days cells infected with Bac.VD143 were shown to have a 5 times higher GFP fluorescence (2.5 a.u.) as compared to the same amount of cells infected with Bac.VD142 (0.5 a.u).

Example 2

Enhanced Transgene Expression in SF+ Cells by Co-Expression of the AAV-Rep Protein 2.1 Materials and Methods
2.1.1 Generation of Baculovirus Plasmids pVD43 and pVD88 were used to prepare recombinant baculovirus stocks (resp. Bac.VD43 and Bac.VD88). The VD43 construct contains the CMV-LPL-WPRE-polyA expression unit between the two AAV2 ITR's. The VD88 construct contains the AAV2 Rep78/52 ORF (modified at the Rep78 initiation codon ATG to ACG) under the control of the PolH insect cell promoter.

2.1.2 Amplification of the AAV Vector Genome

Passage 4 working seed virus was used to generate passage 5 baculovirus inoculum of Bac.VD43 and Bac.VD88. The inoculum was used to infect in log phase growing SF+ insect cells at a cell density of 2E+6 cells/mL with either Bac.VD43 alone or a mixture of Bac.VD43 and Bac.VD88. Three days following infection the cell cultures were harvested with lyses buffer and the clarified crude lysate was immediately subjected to Q-PCR assay in order to determine the CMV copy number.

2.1.3 Determination of the AAV Vector Genome Copy Number

Following AAV vector genome production the lysed cultures were immediately subjected to a Q-PCR assay using primers directed to the CMV promoter. In order to prevent degradation of the produced vector DNA samples of the lysed cultures were not treated with Benzonase and during the Q-PCR procedure the DNase step was eliminated.

2.2 Results

Figure 3:
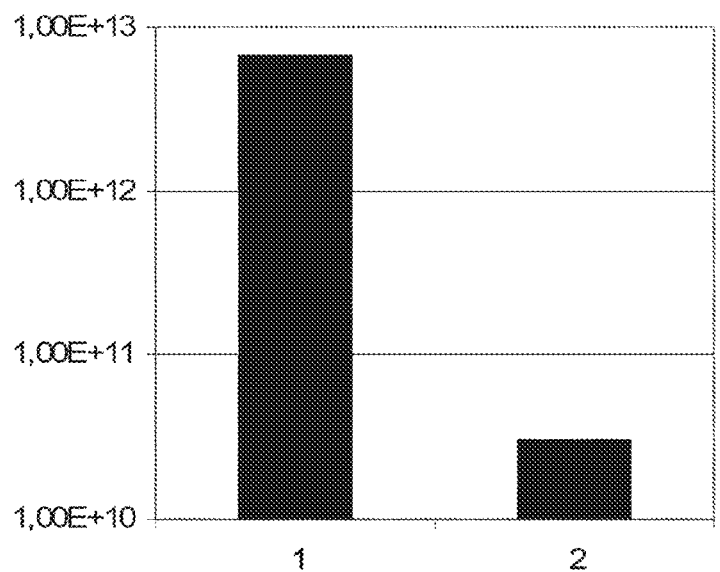
FIG. 3: Increase of the vector genome copy number by AAV-Rep-induced replication of a CMV-LPL transgene unit flanked by AAV-ITR's (Bar 1), compared to baculovirus-induced replication of the vector genome harbored in recombinant baculovirus alone (Bar 2).

FIG. 3 shows vector copynumbers in insect cells infected with either Bac.VD43+Bac.VD88 (Bar 1) or Bac.VD43 alone (Bar 2). 3 days post infection cells were harvested and vector copy numbers were measured by Q-PCR. AAV-Rep-induced replication (Bac.VD88) of the CMV-LPL transgene unit flanked by AAV-ITR's (Bac.VD43) resulted in a more than 200-fold increase of the vector genome (CMV-LPL-WPRE-plyA) copy number compared to baculovirus-induced replication of the vector genome harbored in recombinant baculovirus (Bac.VD43) alone.

Example 3

Increased Viability of SF+ Cells by Co-Expression of the AAV-Rep Protein 3.1 Materials and Methods
3.1.1 Cell Density Determination Viable cell density of insect cells following infection with baculovirus was determined with a Nucleocounter.

3.1.2 Virus

In the experiment two recombinant baculoviruses were compared. One baculovirus harbouring an expression cassette for the transgene LPL and a baculovirus harbouring an expression cassette for the AAV2 Rep ORF:
- Virus WSV bank Bac.VD88 P4 Lot# P.536.00102.01 (Baculovirus harbouring AAV Rep-expression cassette)
- Virus WSV bank Bac.VD43 P4 Lot# P.536.00100.01 (Baculovirus harbouring an expression cassette for a gene of interest, i.e. LPL)

3.1.3 Cells

ExpresSF+® cells were seeded at 1E6 cells/mL in 500 ml Shaker flasks and incubated for 17 hours at 28° C., 135 rpm in a New Brunswick Innova 44R shaker incubator (MF-SIN-2002-s00). These cultures were seeded using SF900 II medium (Invitrogen).

3.1.4 Infection

In the experiment Bac.VD43 or Bac.VD88 were infected either alone or in combination on SF+ cells. Infection occurred using a virus volume versus cell culture volume of 1:333.

3.2 Results

Prior to addition of the recombinant baculovirus stocks (Bac.VD43, Bac.VD88 or Bac.VD43+Bac.VD88) a cell count was performed and viabilities were determined using a NucleoCounter (ENS: RD-SNC-0001-s00) according to GEN-SOP-SNC-8000 (version 03). The culture medium contained 2.14E6 viable cells/mL with a viability of 99.7%. Approximately 70 hours after infection of the SF+ cells with Baculovirus constructs, cell counts were performed and viabilities were determined again.

Table 1 shows that infection of Bac.VD43 harbouring an expression cassette of interest (i.e. LPL under the control of a CMV promoter) results in an increasing cell death over a period of 70 hours. After 70 hours virtually no cells are still viable. However, if the cells are infected with Bac.VD88 harbouring an expression cassette for the AAV Rep the cell death is slowed down and results in a viable cell density of 86% at 70 hours post-infection. This suggests that the AAV Rep protein following expression in insect cells has an anti-apoptotic function. In addition, the results show that infection of the cells with both Bac.VD43 and Bac.VD88 can slow down the cell death (61% versus 0% viability) which normally occurs if cells are only infected by Bac.VD43. This demonstrates that co-infection of a baculovirus harbouring a transgene of interest with a baculovirus expressing a parvoviral Rep protein (Bac.VD88) prolongs the production phase for the transgene of interest and subsequently increase production yield.

This observation is remarkable since the expression of the AAV Rep protein in mammalian cells has so far always been associated with the induction of apoptosis of cells. For insect cells this phenomenon has not yet been described.

TABLE 1

Bac.VD43, Bac.VD88 or Bac.VD43 and Bac.VD88 were infected on SF+ cells and viable cell densities were monitored at 70 hours post-infection.

| Construct | Viable cell density (cells/mL) | Total cell density (cells/mL) | Viability (%) |
| --- | --- | --- | --- |
| Bac.VD43 | 0 | 1.47E+06 | 0 |
| Bac.VD43 + Bac.VD88 | 2.30E+06 | 3.35E+06 | 61.7 |
| Bac.VD88 | 2.94E+06 | 3.45E+06 | 86.5 |

Example 4

Enhanced Protein Expression in Mammalian Cells by Co-Expression of the AAV-Rep Protein 4.1 Materials and Methods 4.1.1 Generation of Plasmids Plasmid pVD179 contains the secreted alkaline phosphatase (SEAP) expression cassette under control of the CMV promoter and is flanked by viral ITRs. This plasmid was constructed by cloning the SEAP expression cassette from pSEAP2-Control (Clontech Laboratories Inc.) into pVD43. Briefly, pSEAP2-Control was digested with EcoRI and HpaI and the 1694 bp fragment was blunted, purified and ligated into blunted pVD43 plasmid from which the LPL-WPRE cassette was deleted with a RsrII digestion. Plasmid pVD203 contains the AAV2 Rep expression cassette under control of the AAV2 p5 promoter and was constructed by deleting the AAV8 capsid expression cassette from p5E18-VD2/8 with an EcoNI and PmeI digestion, blunting the 5' overhangs and re-ligating the plasmid.

4.1.2 Transfection of Mammalian Cells

HeLa cells were cultured in Dulbecco's Modified Eagle's Medium (DMEM, Invitrogen) supplemented with 10% foetal bovine serum and grown at 37° C. with 5% $CO_2$. Cells were seeded at a density of 2E5 cells/well of a 24 wells plate one day before being transfected using polyethylene-imine (PEI, MW ~25000, Polysciences Inc.). For each well 3.0 μl of PEI (1 μg/μl) was added to 50 μl 150 mM NaCl containing 0.5 μg pVD179 and 0.5 μg staffer DNA or 0.5 μg pVD203, and after immediately vortexing the transfection mixture was incubated for 10 min at RT. Medium in the wells was replaced with 450 μl fresh culture medium before addition of the transfection mixture to the cells and incubation at 37° C. with 5% $CO_2$.

4.1.3 SEAP Activity Assay

Two and three days after transfection 75 μl of culture medium was removed from the HeLa cells, centrifuged for 10 sec at 12000 g to pellet detached cells and 60 μl of the supernatant was stored at −20° C. SEAP expression was measured with the Great Escape Chemiluminescence kit 2.0 (Clontech Laboratories Inc.) following the manufacturers protocol. In brief, 25 μl of each sample was diluted in 75 μl× Dilution buffer, incubated at 65° C. for 30 min and chilled on ice for 2-3 min. After equilibrating the samples to RT, 100 μl SEAP substrate solution was added to each sample and incubated for 20 min. The chemiluminescence signal was detected with a luminometer at 470 nm for 1 sec.

4.2 Results

Figure 4:
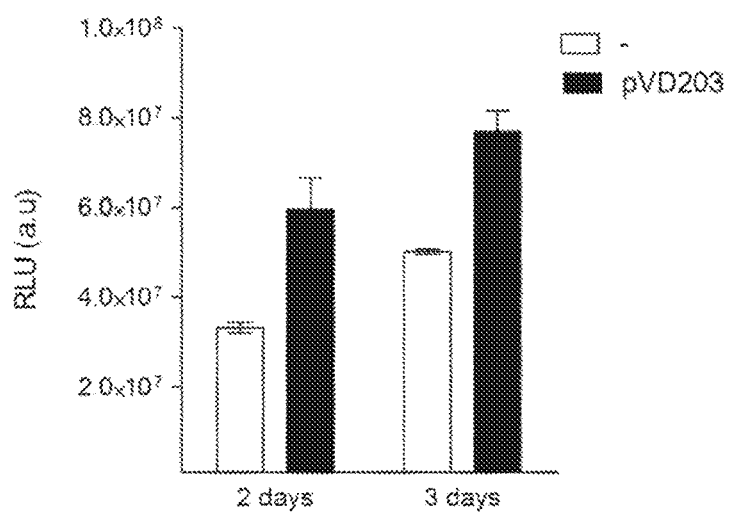
FIG. 4: Enhanced SEAP activity in HeLa cells co-expressing the Rep protein. Two and three days after transfection SEAP activity was measured in the culture medium of HeLa cells transfected with pVD179 (−) or with a combination of pVD179 and pVD203 (pVD203). The experiment was performed in duplo.

FIG. 4 shows SEAP activity in HeLa cells infected with either pVD179 (−) or pVD179+pVD203 (pVD203) 2 and 3 days post transfection. Co-expression of pVD203 (the Rep protein) resulted in a 1.8-fold and 1.5-fold increase of SEAP activity in the medium, respectively, as compared to the cells transfected with only pVD179.

The invention claimed is:

1. An insect cell that comprises:
   (a) a first expression cassette comprising:
      (i) a nucleotide sequence encoding a polypeptide of interest;
      (ii) a promoter operably linked to said coding nucleotide sequence that is capable of driving expression of the polypeptide of interest in the insect cell; and
      (iii) a parvoviral inverted terminal repeat (ITR) nucleotide sequence flanking said expression cassette on both sides;
      and
   (b) a second expression cassette that comprises:
      (i) a nucleotide sequence encoding at least one parvoviral Rep protein; and (ii) a promoter operably linked to said nucleotide sequence encoding said Rep protein that is capable of driving expression of the Rep protein in the insect cell;

which insect cell does not comprise a parvoviral Cap protein or a nucleotide sequence encoding a parvoviral Cap protein, and wherein the expression of the polypeptide of interest is increased, as compared to an insect cell which comprises said nucleotide encoding said polypeptide of interest and said promoter operably linked thereto and said flanking parvoviral ITR sequence but differs in that it does not comprise said nucleotide sequence encoding said at least one parvoviral Rep protein operably linked to said promoter capable of driving expression of the Rep protein in said cell.

2. A method for producing a polypeptide of interest in an insect cell, comprising culturing the insect cell according to claim 1 under conditions that are conducive for expression of the first and the second expression cassettes, thereby attaining said increased expression and production of said polypeptide of interest.

3. The method according to claim 2 further comprising recovering said polypeptide of interest from the culture.

4. The method according to claim 2, wherein the second expression cassette comprises an open reading frame comprising nucleotide sequences encoding Rep78 and/or Rep68 proteins.

5. The method according to claim 2, wherein the first and the second expression cassettes are present in a single construct that is flanked by a parvoviral ITR sequence on each side.

6. The method according to claim 2, wherein the parvoviral ITR sequence and parvoviral Rep protein are from an adeno-associated virus.

7. The method according to claim 2, wherein at least one of the expression cassettes is comprised in a baculoviral vector.

* * * * *